(12) United States Patent
Rayhanabad

(10) Patent No.: US 12,161,545 B1
(45) Date of Patent: Dec. 10, 2024

(54) MODULAR AORTIC STENT-GRAFT WITH BRANCH EXTENSIONS AND ENDOVASCULAR METHOD OF REPAIRING AN AORTIC ANEURYSM WITH A MODULAR STENT-GRAFT

(71) Applicant: SBR Innovations, LLC, Huntington Beach, CA (US)

(72) Inventor: Simon B. Rayhanabad, Huntington Beach, CA (US)

(73) Assignee: SBR Innovations, LLC, Huntington Beach, CA (US)

( * ) Notice: Subject to any disclaimer, the term of this patent is extended or adjusted under 35 U.S.C. 154(b) by 0 days.

(21) Appl. No.: 18/431,963

(22) Filed: Feb. 3, 2024

Related U.S. Application Data

(60) Provisional application No. 63/483,509, filed on Feb. 6, 2023.

(51) Int. Cl.
| | |
|---|---|
| *A61F 2/07* | (2013.01) |
| *A61F 2/954* | (2013.01) |
| *A61F 2/962* | (2013.01) |
| *A61F 2/06* | (2013.01) |
| *A61L 27/06* | (2006.01) |
| *A61L 27/14* | (2006.01) |

(52) U.S. Cl.
CPC ............... *A61F 2/07* (2013.01); *A61F 2/954* (2013.01); *A61F 2/962* (2013.01); *A61F 2002/067* (2013.01); *A61F 2210/0014* (2013.01); *A61F 2220/0025* (2013.01); *A61F 2230/006* (2013.01); *A61F 2250/0004* (2013.01); *A61F 2250/0006* (2013.01); *A61F 2250/0008* (2013.01); *A61F 2250/006* (2013.01); *A61L 27/06* (2013.01); *A61L 27/14* (2013.01)

(58) Field of Classification Search
CPC .. A61F 2250/006–0064; A61F 2/07–2002/075
See application file for complete search history.

(56) References Cited

U.S. PATENT DOCUMENTS

| | | | |
|---|---|---|---|
| 6,733,523 B2 * | 5/2004 | Shaolian | A61F 2/856 623/1.3 |
| 11,534,286 B1 | 12/2022 | Rayhanabad | |
| 2007/0055350 A1 * | 3/2007 | Erickson | A61F 2/07 623/1.16 |
| 2009/0216315 A1 * | 8/2009 | Schreck | A61F 2/954 623/1.35 |
| 2022/0211483 A1 | 7/2022 | Rayhanabad | |

OTHER PUBLICATIONS

Co-pending and commonly owned U.S. Appl. No. 18/587,878, filed Feb. 26, 2024.

* cited by examiner

*Primary Examiner* — Rebecca S Preston
(74) *Attorney, Agent, or Firm* — Steven R. Vosen

(57) ABSTRACT

A modular aortic stent-graft is configured to fit in an abdominal aorta near an aneurysm, the left and right renal arteries and the left and right iliac arteries and may be used to treat an aneurysm. The aortic stent-graft includes three stent-graft portions which, when provided to a patent, form the aortic stent-graft. The aortic stent-graft is capable of fitting into a range of renal artery locations along the abdominal artery. An endoscopic method provides for providing the aortic stent-graft to a patient in a minimally invasive manner.

14 Claims, 18 Drawing Sheets

MODULAR AORTIC STENT-GRAFT WITH BRANCH EXTENSIONS AND ENDOVASCULAR METHOD OF REPAIRING AN AORTIC ANEURYSM WITH A MODULAR STENT-GRAFT

CROSS-REFERENCE TO RELATED APPLICATIONS

This application claims the benefit of U.S. Provisional Application No. 63/483,509, filed Feb. 6, 2023, the contents of which are hereby incorporated by reference in its entirety.

BACKGROUND OF THE INVENTION

Field of the Invention

The present invention generally relates to medical devices, and more particularly to a modular aortic stent-graft with branch extensions and a method of providing a modular aortic stent-graft with branch extensions to repair an aortic aneurysm.

Discussion of the Background

The repair of aortic aneurysms is typically performed by a surgical procedure or by a minimally invasive procedure. The goal of these procedures is to provide support to the aortic wall, preventing the aneurysm from rupturing and reducing the risk of death.

Surgical procedures involve the surgeon performing the following steps: making an incision in the chest or abdomen to access the aneurysm; replacing the affected section of the aorta with a synthetic tube designed to mimic the normal structure and function of the aorta; and closing the incision.

Minimally invasive procedures, such as Endovascular Aneurysm Repair (EVAR), is typically performed using a wire and catheter-based approach and involves the surgeon performing the following steps: making a small incision in the groin area to access the femoral artery; inserting a catheter into the femoral artery; guiding the catheter to the site of the aneurysm using X-ray imaging; deploying a stent-graft at the site of the aneurysm to support the weakened aortic wall and prevent further expansion of the aneurysm; and anchoring the stent-graft in the aortic wall using small hooks or barbs; and removing the catheter and closing the incision in the groin.

Open surgical repair is more invasive and requires a longer recovery time compared to EVAR. The risk of complications such as bleeding, infection, and injury to surrounding organs is higher with open surgical repair.

The problems associated with EVAR include: the stent-graft can become dislodged or shift, which can require another procedure to reposition it; the stent-graft can develop a leak, which can cause significant problems and require another procedure to fix; the stent-graft can become occluded, which can reduce or block blood flow to the legs or kidneys.

There is a need in the art for less invasive methods of repairing aortic aneurysms and for medical devices that support such procedures. In addition, such devices should allow the surgeon to repair aortic aneurysms for a range of anatomical configurations, such as the location of the left renal artery relative to the right renal artery.

BRIEF SUMMARY OF THE INVENTION

The present invention overcomes the disadvantages of the prior art by providing a modular aortic stent-graft. In certain embodiments, the inventive modular stent-graft is deployed in a patient in a minimally invasive procedure that, when assembled within the circulatory system of the patient, extends from the abdominal aorta and into the left and right renal arteries and the left and right iliac arteries. This stent-graft geometry is more complex and useful for the repair of aortic aneurysms that prior art stent-grafts. In addition, by extending into the renal and iliac arteries, the deployed stent-graft is more stable than prior art stent-grafts.

The present invention also overcomes the disadvantages of the prior art by providing an aortic stent-graft having extensions for the renal arteries whose relative position relative to the aorta are adjusted during the insertion of the stent-graft portions into the arteries. This allows a single collection of stent-graft portions to be useful for a range of anatomical configurations.

It is one aspect of the invention to provide a modular stent-graft sized to fit in an abdominal aorta, a left renal artery, a right renal artery, a left iliac artery, and a right iliac artery of a person. The modular stent-graft includes: three portions including a first portion, a second portion, and a third portion, where each of the first portion, the second portion, and the third portion includes a stent-graft sized to be delivered through either the left iliac artery or the right iliac artery and adapted to be deployed within the abdominal aorta, the left renal artery, the right renal artery, the left iliac artery, or the right iliac artery. The modular stent-graft includes a main body sized to fit in the abdominal aorta, a right upper branch of the main body sized to fit in the right renal artery, a left upper branch of the main body sized to fit in the left renal artery, a left lower branch of the main body sized to fit in the left iliac artery, and a right lower branch of the main body sized to fit in the right iliac artery.

It is another aspect of the invention to provide an adjustable modular stent-graft including a main body sized to fit in an abdominal aorta of a person, a right upper branch of the main body sized to fit in a right renal artery of the person, and a left upper branch of the main body sized to fit in a left renal artery of the person. The adjustable modular stent-graft includes two portions including a first portion and a second portion, where the first portion includes the main body, the right upper branch, and a first portion aperture in the main body opposite from the right upper branch, where the second portion includes a second portion main body sized to fit within the first portion main body, the left upper branch which extends through the first portion aperture, and a second portion aperture in the second portion main body positioned to not occlude the right upper branch, and where a longitudinal position of the right upper branch and the left upper branch along the main body is adjustable according to size and location of the first portion aperture and the second portion aperture.

It is yet another aspect of the invention to provide a method for repairing an aortic aneurysm of a person with a modular stent-graft sized to fit within an abdominal aorta, a right renal artery, a left renal artery, a left iliac artery, and a right iliac artery of the person, where the modular stent-graft includes three overlapping portions including a first portion, a second portion, and a third portion. The method includes: a first incising of a left groin and the left iliac artery of the person; a second incision of a right groin and the right iliac artery of the person; deploying the first portion through the first incision to the abdominal aorta at the aneurysm and to the right renal artery; deploying the second portion through the first incision and interior to the first portion and to the left renal artery; and deploying the third portion through the second incision and interior to the first portion and to the right iliac artery.

It is one aspect of the invention to provide a method for repairing an aortic aneurysm of a person with a modular stent-graft sized to fit within an abdominal aorta, a right renal artery, a left renal artery, a left iliac artery, and a right iliac artery of the person, where the modular stent-graft includes three overlapping portions including a first portion, a second portion, and a third portion, where the modular stent-graft includes a main body sized to fit in the abdominal aorta, a right upper branch of the main body sized to fit in the right renal artery, a left upper branch of the main body sized to fit in the left renal artery, a left lower branch of the main body sized to fit in the left iliac artery, and a right lower branch of the main body sized to fit in the right iliac artery, where the first portion includes the main body, the right upper branch, and a bifurcation of the main body to form the left lower branch and a first portion branch extending towards the right iliac artery, where the second portion includes a second portion main body sized to fit within the main body, the left upper branch, and where the third portion includes a third portion main body sized to fit in the first portion branch, where the third portion includes the right lower branch. The method includes: a first incising of a left groin and the left iliac artery of the person; a second incision of a right groin and the right iliac artery of the person; deploying the first portion through the first incision to the abdominal aorta at the aneurysm and to the right renal artery; deploying the second portion through the first incision and to an interior of the deployed main body and to the left renal artery; and deploying the third portion through the second incision and to an interior of the deployed first portion branch and to the right iliac artery.

It is another aspect of the invention to provide a method for repairing an aortic aneurysm of a person with a modular stent-graft sized to fit within an abdominal aorta, a right renal artery, a left renal artery, a left iliac artery, and a right iliac artery of the person, where the modular stent-graft includes three overlapping portions including a first portion, a second portion, and a third portion, where the first portion includes a first portion main body sized to fit in the abdominal aorta, a first portion branch from the first portion main body adapted to fit in the right renal artery, and a first portion aperture in the first portion main body positioned on opposite from the first portion main body from the first portion branch, and a bifurcation of the main body to form a portion of a lower left branch adapted to fit in the left iliac artery and a lower right branch adapted to fit in the right iliac artery, where the second portion includes a second portion main body sized to fit in the main body of the first portion, a second portion branch from the second portion main body, where the second portion branch is adapted to fit in the left renal artery, and a second portion aperture in the second portion main body positioned on opposite from the second portion main body from the second portion branch, and where the third portion includes a main body sized to fit the into the portion of the lower right branch of the first portion and positioned to fit in the right iliac artery. The method includes: a first incising of a left groin and the left femoral artery of the person; a second incising of a right groin and the right femoral artery of the person; deploying the first portion through the first incision with the first portion main body along the abdominal aorta at the aneurysm, with the first portion branch in the right renal artery, with the lower right branch extending towards the right iliac artery, and with the lower left branch extending towards the left iliac artery; deploying the second portion through the first incision with the second portion main body within the first portion main body, with the second portion branch extending through the first portion aperture and into the left renal artery, and with the second portion aperture not occluding the first portion branch; and deploying the third portion through the second incision with the third portion main body within the lower right branch with the third portion main body extending into the right iliac artery.

These features together with the various ancillary provisions and features which will become apparent to those skilled in the art from the following detailed description, are attained by the aortic stent-graft and method of the present invention, preferred embodiments thereof being shown with reference to the accompanying drawings, by way of example only, wherein:

Reference symbols are used in the Figures to indicate certain components, aspects or features shown therein, with reference symbols common to more than one Figure indicating like components, aspects or features shown therein.

DETAILED DESCRIPTION OF THE INVENTION

The following description includes the disclosure of an aortic stent-graft and an endoscopic method of repairing an aortic aneurysm. In general, as described subsequently, the aortic stent-graft is adapted to span a length of the abdominal aorta from above the renal arteries to the left and right iliac arteries, and also into the left and right renal arteries. For use in an endoscopic procedure, the aortic stent-graft includes three portions which are assembled within the circulatory system.

Figure 1:
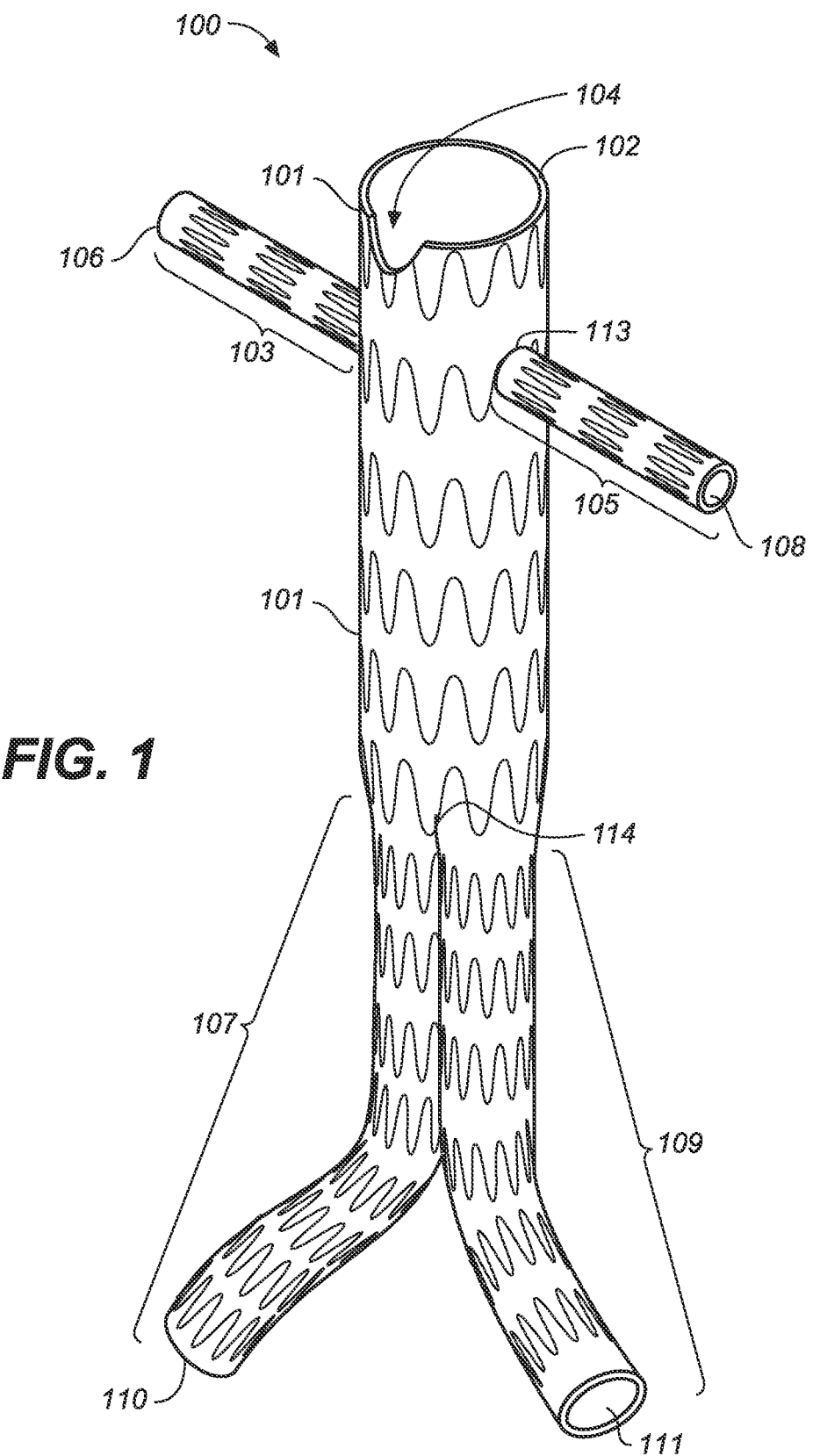
FIG. 1 is a perspective posterior view of a first embodiment aortic stent-graft.

FIG. 1 is a perspective posterior view of a first embodiment modular aortic stent-graft 100 which includes several generally cylindrical portions adapted, that is sized and can be positioned to fit within the abdominal aorta, the left and right renal arteries, and the left and right iliac arteries without obstructing the superior mesenteric artery, as discussed subsequently. In one embodiment, modular aortic stent-graft 100 includes several generally cylindrical stent-graft portions including a main body 101, an upper right branch 103, an upper left branch 105; and a lower right branch 107, and a lower left branch 109, and has a lumen with five openings: a first opening 102, a second opening 106, a third opening 108, a fourth opening 110, and a fifth opening 111. More specifically: main body 101 extends from first opening 102 to a bifurcation 114 of the main body and includes a notch 104 on the posterior side of the main body; upper right branch 103 extends from a right junction 112 at the main body to second opening 106; upper left branch 105 extends from a left junction 113 to third opening 108; lower right branch 107 extends from the bifurcation to fourth opening 110; and lower left branch 109 extends from the bifurcation to fifth opening 111.

In certain embodiments, the modular aortic stent-graft 100 is sized to reinforce the abdominal aorta having an aneurysm, as described subsequently. Thus, for example and without limitation, main body 101 is sized to fit within the abdominal aorta with notch 104 sized and positioned to allow for blood flow from the aorta to the superior mesenteric artery, with upper right branch 103 sized and positioned to fit within the right renal artery, with upper left branch 105 sized and positioned to fit within the left renal artery, with lower right branch 107 sized and positioned to fit within the right iliac artery, and with lower left branch 109 sized and positioned to fit within the left iliac artery.

In certain embodiments, modular aortic stent-graft 100 does not block the flow of blood to the gonadal arteries, but it may block the flow to the lumbar arteries, the inferior mesenteric artery, and the median sacral artery, as happens with prior art aortic stent-grafts. In certain embodiments, modular aortic stent-graft 100 is sized to fit in the abdominal aorta, and thus, for example and without limitation main body 101 has a diameter to fit within the abdominal aorta and is from approximately 1.5 cm to approximately 40 cm, upper right branch 103 is sized to fit within the right renal artery and has a diameters of approximately 3 mm to approximately 7 mm, upper left branch 105 is sized to fit within the left renal artery and has a diameter of approximately 3 mm to approximately 25 mm, lower right branch 107 is sized to fit within the right iliac artery and has a diameter of from approximately 6 mm to approximately 25 mm, and lower left branch 109 is sized to fit within the left iliac artery and has a diameter of from approximately 6 mm to approximately 25 mm. The length of upper right branch 103 from a right junction 112 at main body 101 to second opening 106 is from 1.5 cm to 4 cm, the length of upper left branch 105 from a left junction 113 to third opening 108 is from 1.5 cm to 4 cm, the distance from first opening 102 to bifurcation 114 is from 5 cm to 14 cm, the length of lower right branch 107 from the bifurcation to fourth opening 110 is from 10 cm to 16 cm, and the length of lower left branch 109 from the bifurcation to fifth opening 111 is from 10 cm to 16 cm.

Modular aortic stent-graft 100 maybe formed, for example and without limitation, from expandable biocompatible components which each include a metal framework or mesh formed, for example and without limitation, from a metal alloy such as nickel titanium, covered by a thin fabric formed, for example and without limitation, from a polyester, which may be, for example and without limitation, an expanded polytetrafluoroethylene (ePTFE), as is known in the art of stent-grafts. Modular aortic stent-graft 100 is thus a collapsible and self-expanding structure that, when deployed in a patient, can provide a barrier to the flow fluids, such as blood. In certain embodiments, modular aortic stent-graft 100 thus forms a lumen that provides for fluid flow between first opening 102, second opening 106, opening 108, fourth opening 110, and fifth opening 111.

Figure 2:
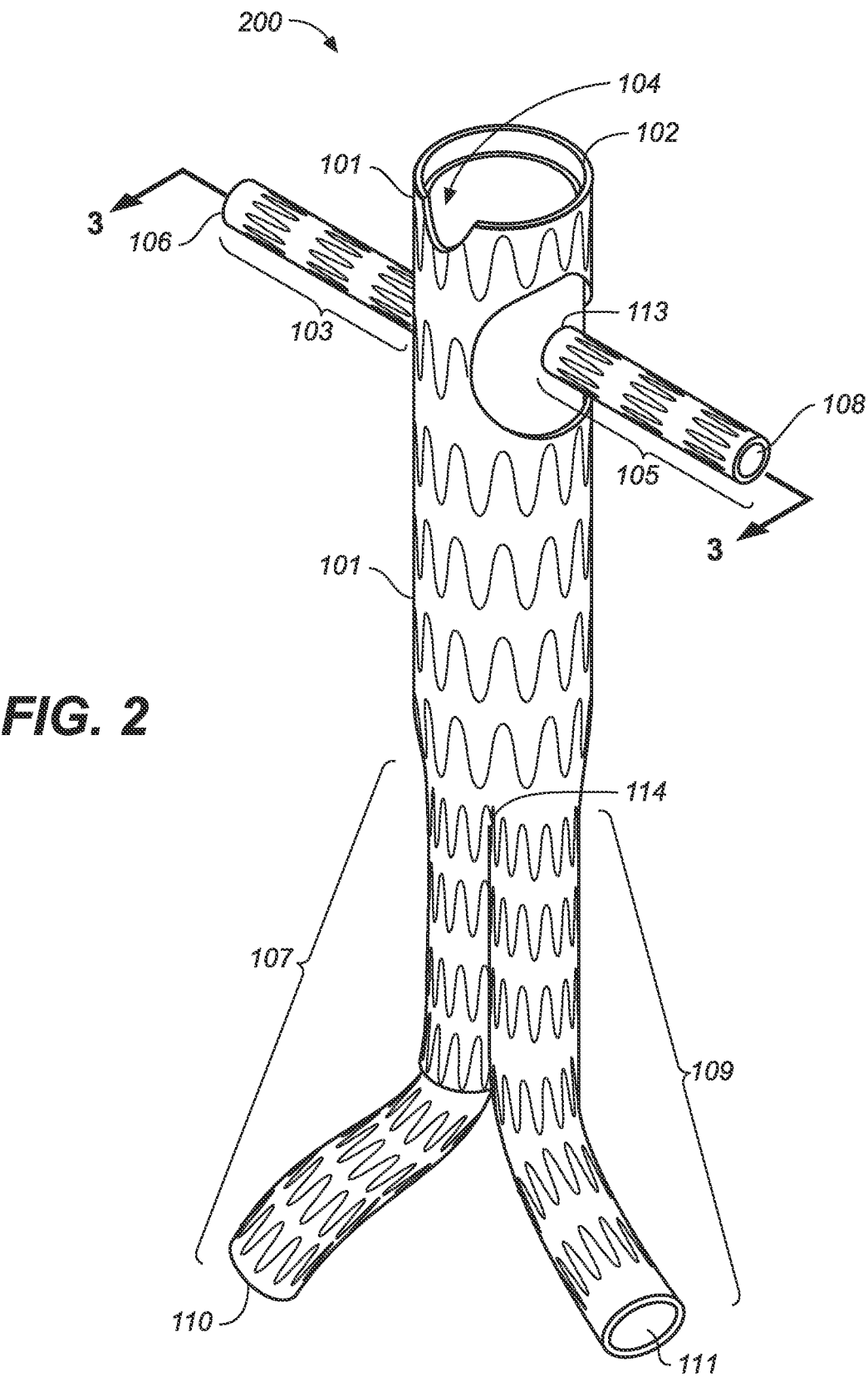
FIG. 2 is a perspective posterior view of a second embodiment aortic stent-graft.
Figure 3:
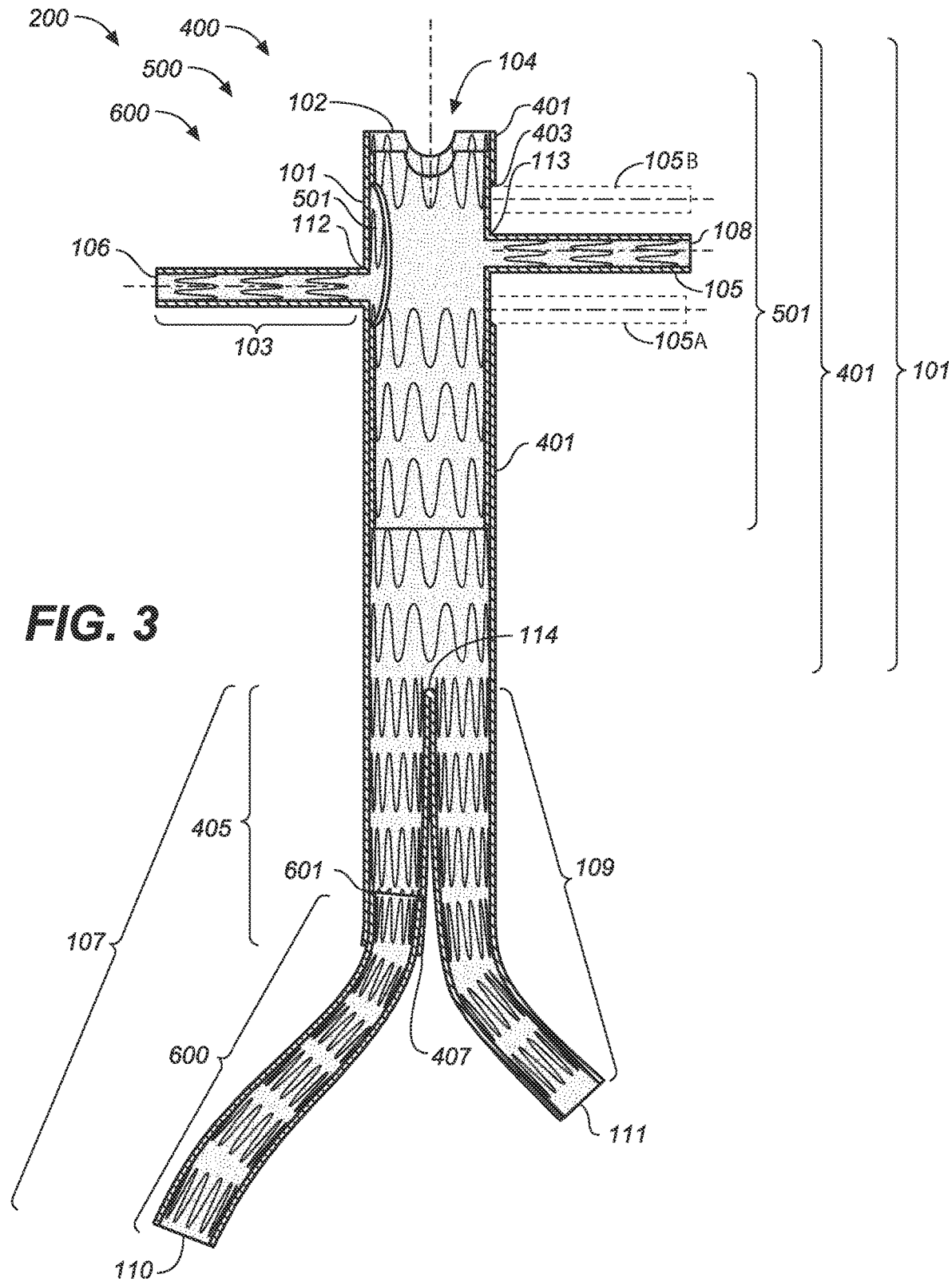
FIG. 3 is a sectional view 3-3 of the aortic stent-graft of FIG. 2.

FIG. 2 is a perspective posterior view of a second embodiment modular aortic stent-graft 200 and FIG. 3 is a sectional view 3-3 of FIG. 2, where aortic stent-graft 200 is generally similar to modular aortic stent-graft 100, except as explicitly stated.

Aortic stent-graft 200 is formed, for example and without limitation, from one or more mutually overlapping stent-graft portions, where the shape of the overlapping stent-graft portions of modular aortic stent-graft 200 is generally the same as the shape of modular aortic stent-graft 100.

Figure 4:
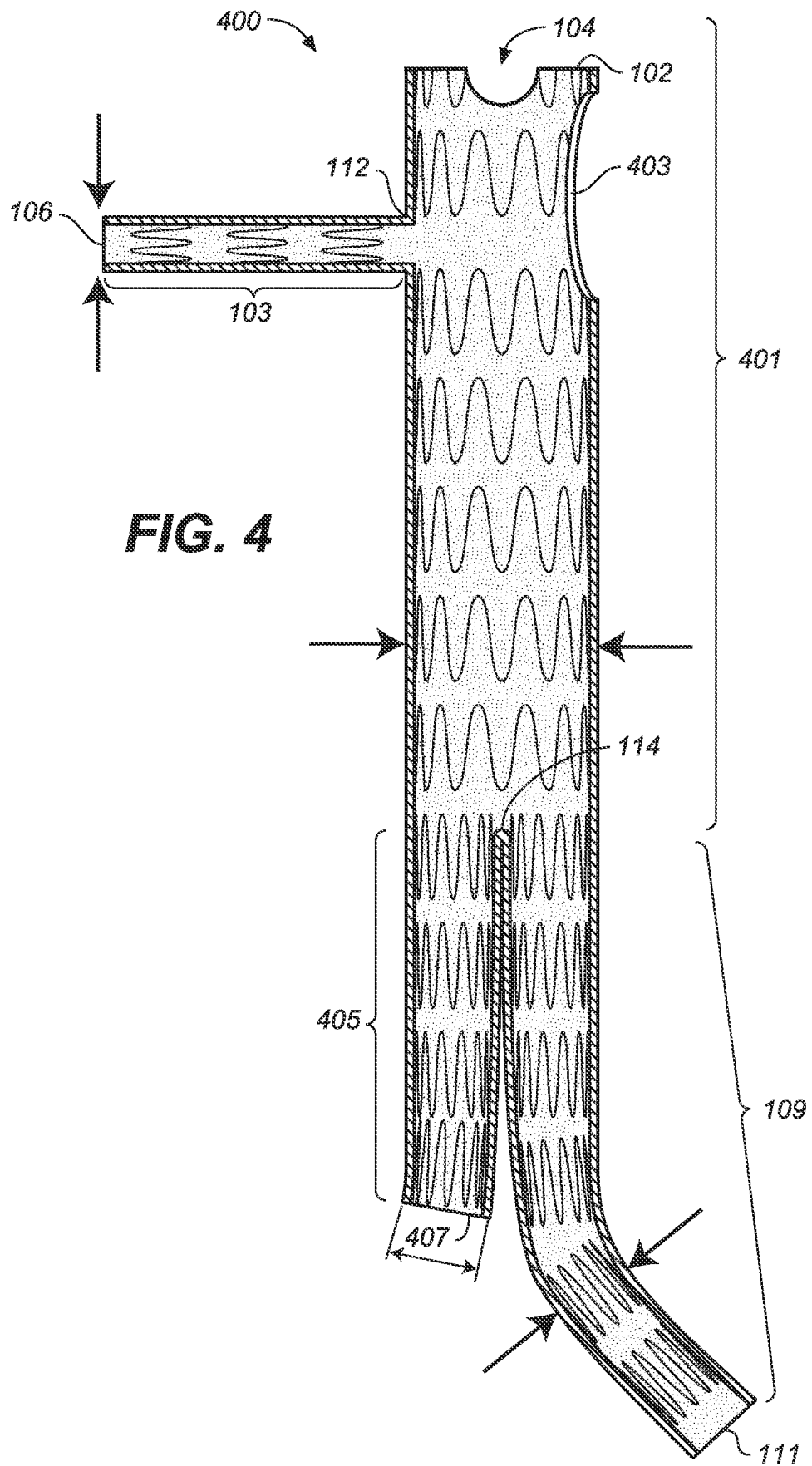
FIG. 4 is a sectional view 3-3 of a first portion of the aortic stent-graft of FIG. 2.

Aortic stent-graft 200, as discussed below, is formed from three portions including a first portion 400, a second portion 500, and a third portion 600. FIG. 4 as a sectional posterior side view 3-3 of first portion 400, FIG. 5 as a sectional posterior side view 3-3 of second portion 500, and FIG. 6 as a sectional posterior side view 3-3 of a third portion 600.

As described subsequently, first portion 400, second portion 500, and third portion 600, are generally cylindrical lumens, each of which may be formed from a metal framework or mesh formed from a metal alloy such as nickel titanium, covered by a thin fabric formed from a polyester, such as expanded polytetrafluoroethylene (ePTFE), and example and without limitation, one or more of main body 101, upper right branch 103, upper left branch 105, lower right branch 107, or lower left branch 109 may be formed from overlapping portions of first portion 400, second portion 500, and third portion 600, where the forces of the metal framework and/or forces from an aorta into which they are placed maintain the structure of modular aortic stent-graft 100.

As shown in FIGS. 3 and 4, first portion 400 includes a main body 401 that extends from first opening 102 to bifurcation 114 with upper right branch 103 extending from right junction 112 to second opening 106 and includes notch 104 at first opening 102 and an upper left aperture 403 on the opposite side of the main body from the upper right branch, a lower right branch 405 that extends from the bifurcation to an opening 407, and lower left branch 109 that extends from the bifurcation to fifth opening 111.

Figure 5:
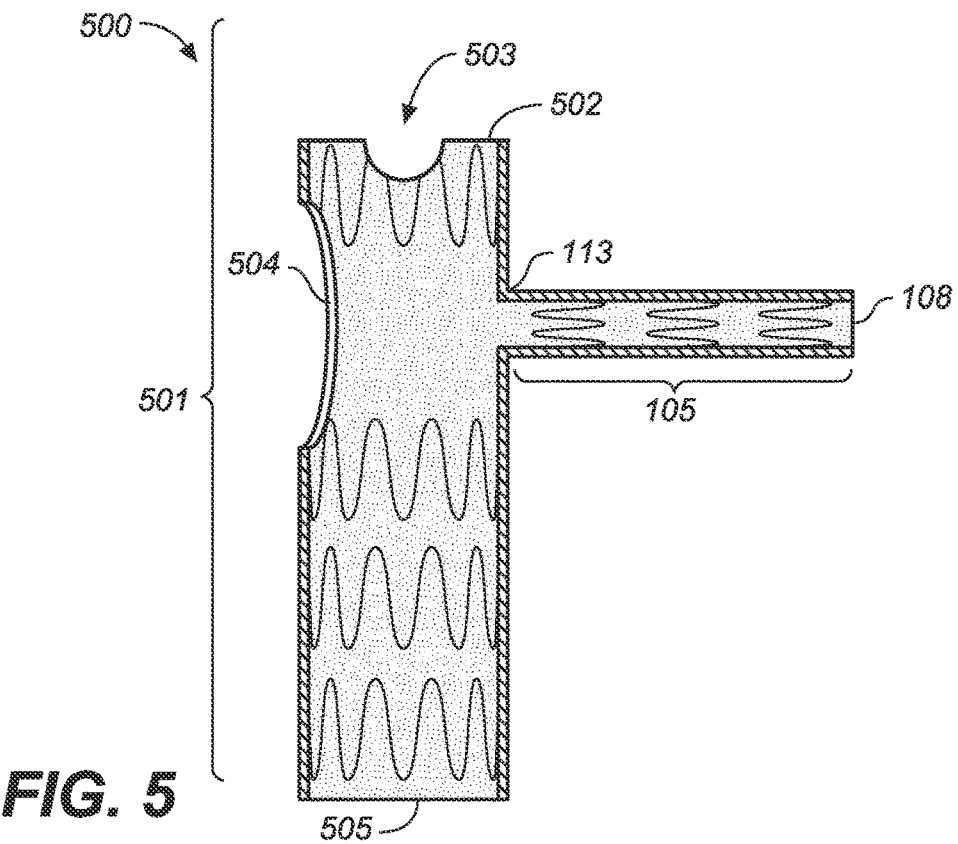
FIG. 5 is a sectional view 3-3 of a second portion of the aortic stent-graft of FIG. 2.

As shown in FIGS. 3 and 5, second portion 500 includes a main body 501 that extends from an opening 505 to an opening 502 that includes a notch 503 on the posterior side of main body 501, upper left branch 105, an upper right aperture 504 on the opposite side of the main body from the upper left branch. As shown in FIG. 3, main body 501 is located within an interior of main body 401 and upper left branch 105 of second portion 500 extends through upper left aperture 403 of first portion 400 and upper right aperture 504 or second portion 500 is positioned to not occlude right junction 112, and thus forming a lumen that extends from first opening 102 to second opening 106 and third opening 108.

Figure 6:
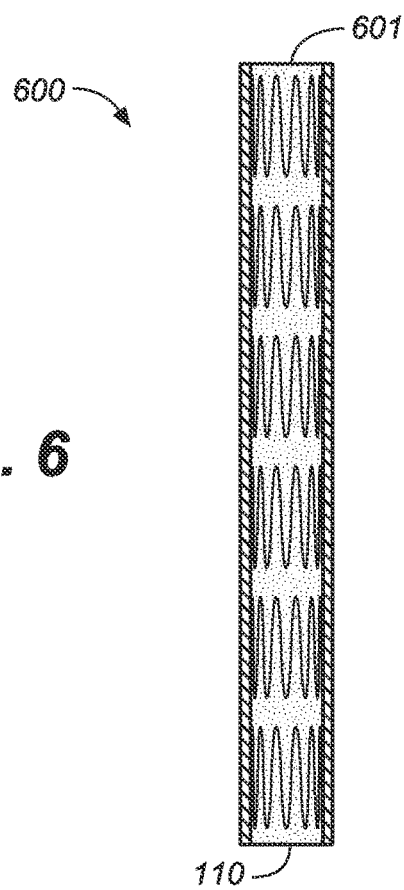
FIG. 6 is a sectional view 3-3 of a third portion of the aortic stent-graft of FIG. 2.

As shown in FIGS. 3 and 6, third portion 600 extends from an opening 601 to fourth opening 110, with the opening within the interior of lower right branch 405.

Thus, as shown in FIGS. 2-6: 1) main body 101 is thus formed from an overlap of main body 401 of first portion 400 and main body 501 of second portion 500, with the upper left branch 105 of the second portion protruding through upper left aperture 403 of the first portion and with right junction 112 aligning with upper right aperture 504 of the second portion to provide fluid communication between first opening 102 and second opening 106; 2) upper right branch 103 is formed from a part of first portion 400; 3) upper left branch 105 is formed from a part of second portion 500; 4) lower right branch 107 is formed from third portion 600 and a part of first portion 400; and 5) lower left branch 109 is formed from a portion of first portion 400.

In certain embodiments, the sizing and placement of upper left aperture 403, upper left branch 105, upper right aperture 504 and upper right branch 103 permits a range of longitudinal displacement of upper right branch 103 relative to upper left branch 105. Thus, for example FIG. 3 shows a range of possible positions of upper left branch 105 including a lower position as upper left branch 105A and an upper position as an upper left branch 105B. In various embodiments, upper left branch 105 can be positioned above upper right branch 103, as shown by upper left branch 105 or upper left branch 105B, or can be positioned below the upper right branch, as shown in upper left branch 105A. It is obvious to those skilled in the art that the range of longitudinal displacements of upper right branch 103 and upper left branch 105 are possible according to the size and placement of upper left aperture 403 and upper right aperture 504. The ability to adjust the longitudinal displacement of upper right branch 103 and upper left branch 105 is, under certain circumstances, important since the longitudinal position of the left and right renal arteries along the abdominal aorta varies from person to person. Further, since the left renal artery is usually higher up the abdominal aorta than the right renal artery, this is not always the case.

In certain embodiments, for example and without limitation, upper left aperture 403 and upper right aperture 504 are sized such that the distance between the lower position of upper left branch 105A and upper right branch 103 is from 0 mm to 90 mm. In certain other embodiments, for example and without limitation, upper left aperture 403 and upper right aperture 504 are sized such that the distance between the upper position of upper left branch 105B and upper right branch 103 is from 0 mm to 20 mm.

In certain embodiments, the use of aortic stent-graft 200 includes guiding and deploying first portion 400, second portion 500, and third portion 600 to the circulation system of the patent using separate delivery systems that are each delivered using guidewires. Thus, for example and without limitation, each of first portion 400, second portion 500, and third portion 600 is provided in a delivery system similar to the GORE® C3 Delivery system (W. L. Gore & Associates, 555 Paper Mill Road Newark, DE 19711), wherein a stent-graft is compressed in a delivery system that is treaded to a deployment location using guidewires, and where the delivery system moves away from the stent-graft, allowing the stent-graft to expand into position.

Figure 7:
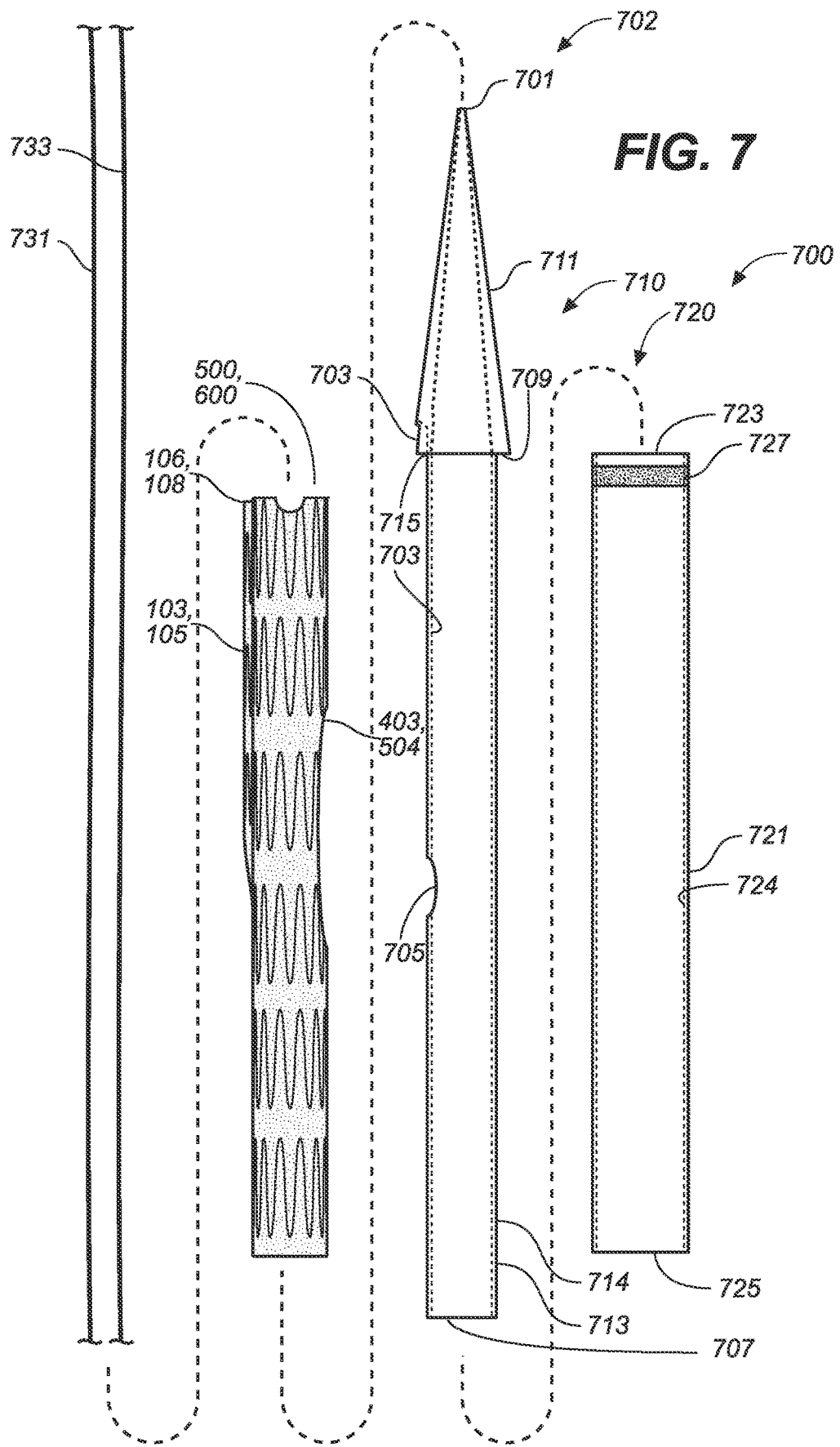
FIG. 7 is an assembly view of a first and second aortic stent-graft portion delivery system.
Figure 8:
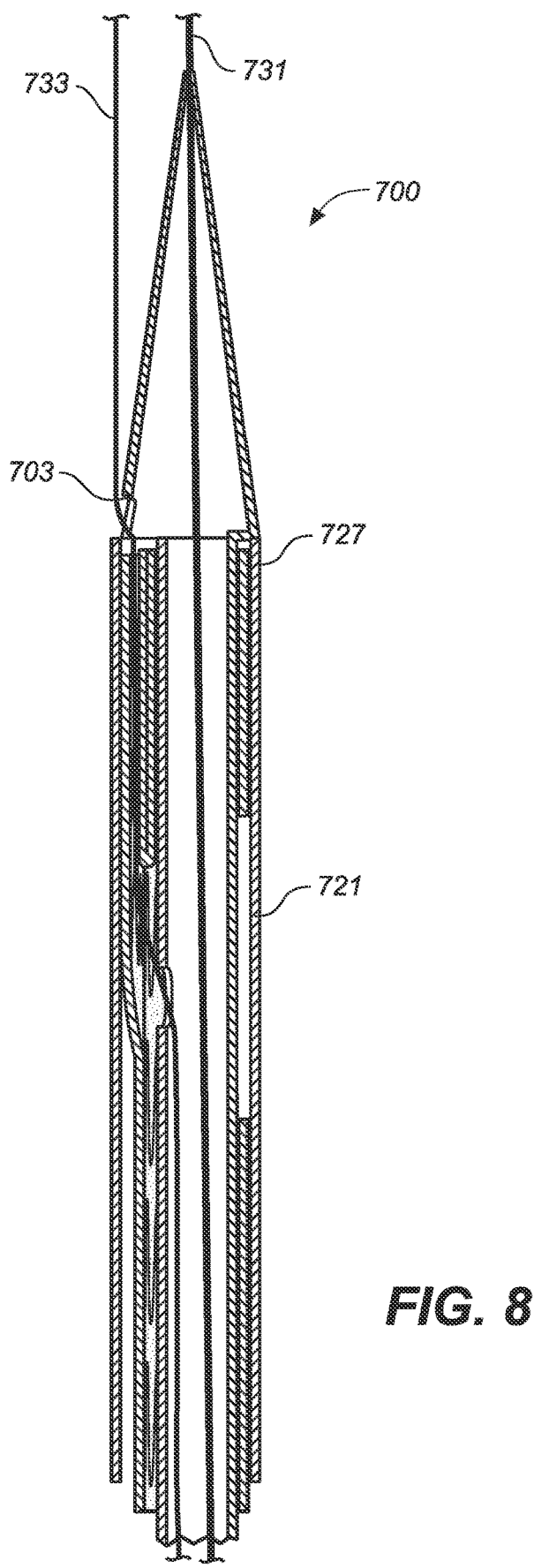
FIG. 8 is a sectional side view of the delivery system of FIG. 7.
Figure 9:
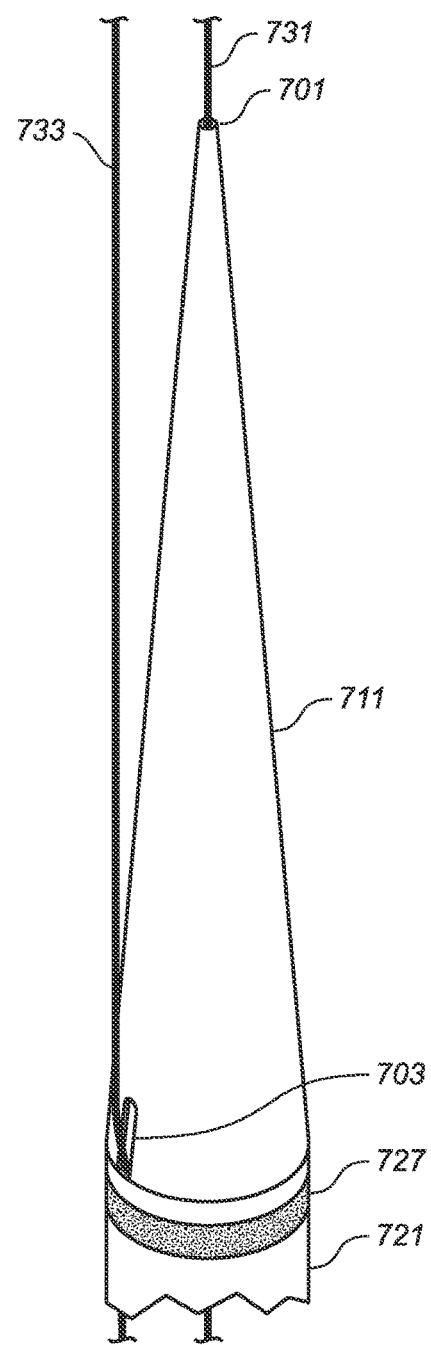
FIG. 9 is a detail perspective posterior view of the delivery system of FIG. 7.
Figure 10:
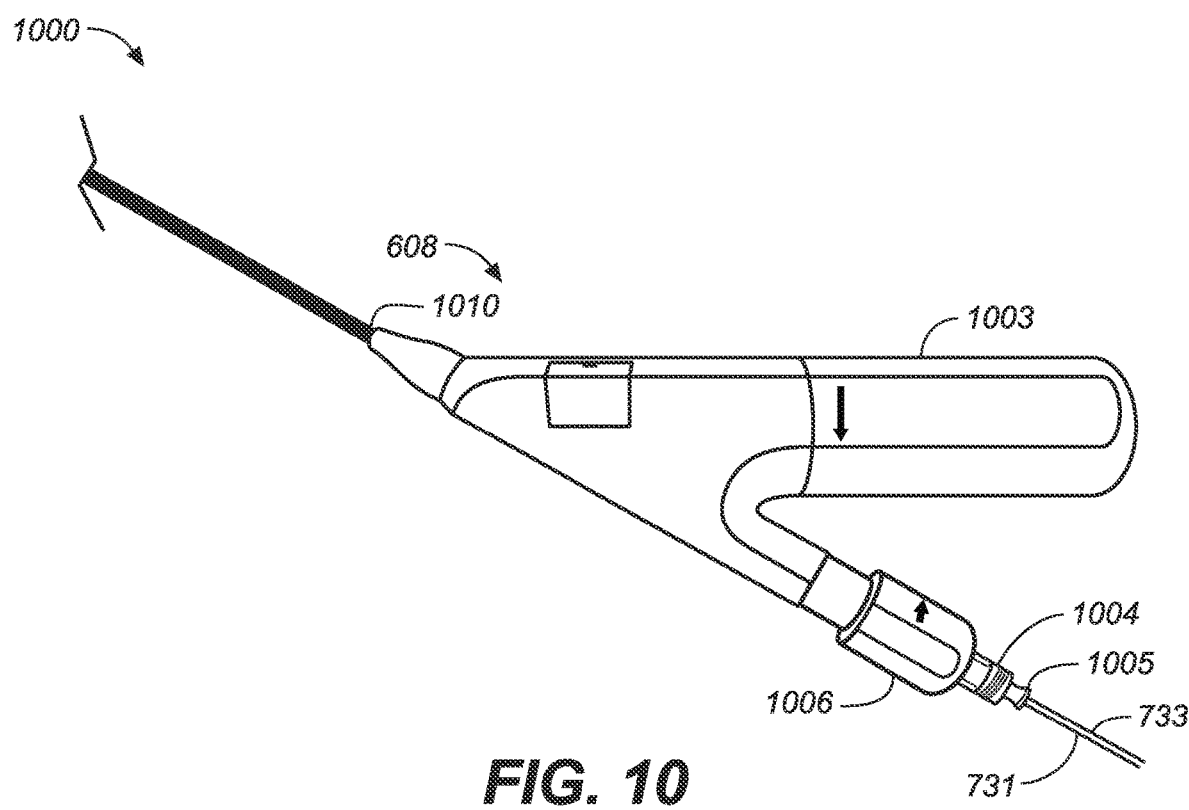
FIG. 10 is side view of the proximal end of the delivery system of FIGS. 7-9.

An example of a first delivery system 700 is illustrated in an assembly view of FIG. 7, in FIG. 8 as a sectional side view of the first delivery system of FIG. 7, in FIG. 9 as a detail perspective view of the delivery system of FIG. 7, and in FIG. 10 as a view of the proximal end of the delivery system of FIG. 7. First delivery system 700 may be used to deliver stent-graft portions having a branch, such as first portion 400 or second portion 500, as discussed subsequently. In certain embodiments, a first of two first delivery systems is used to deliver first portion 400 and a second of two first delivery systems is used to deliver second portion 500.

First delivery system 700 includes a central body 710 and a sleeve 720. Central body 710 has a hollow, cylindrical portion 713 with an outer surface 714 that extends from a proximal end 707 to a distal end 715 with an aperture 705 though the hollow portion, and a hollow, conical cap 711 having a base 709 at distal end 715, a notch 703 at the base, and an opening 701 at the peak of the conical cap. Sleeve 720 extends from proximal end 725 to distal end 723 and has a band 727 on an outer surface 721 and is hollow with inner surface 724. Band 727 is used to assist in the placement of aortic stent-graft 200, as discussed subsequently.

The assembly of first portion 400 and second portion 500 of aortic stent-graft 200 into their respective first delivery system 700 is similar. Thus, for example, first portion 400/second portion 500 is provided to a respective first delivery system 700 with the stent-graft portions compressed within a volume between outer surface 714 of cylindrical portion 713 and inner surface 724 of sleeve 720. Upper left branch 103/upper left branch 105 is aligned such that second opening 106/third opening 108 is near distal end 715, and right junction 112/left junction 113 is aligned to be near aperture 705. First guidewire 731 is inserted through proximal end 707, through the corresponding the main body (main body 401 or main body 501), and through opening 701. Second guidewire 733 is inserted through proximal end 707, through aperture 705, through the corresponding branch, upper right branch 103 or upper left branch 105, and through notch 703.

A grip 1000, as shown in FIG. 10, accepts proximal end 707 of central body 710, proximal end 725 of sleeve 720, first guidewire 731, and second guidewire 733 at grip end 1010, and includes a deployment knob 1003, a Tuohy-Borst valve 1004, a guidewire lumen and flushing port 1005, and an angulation control knob 1006. Grip 1000 is similar to GORE® C3 Delivery system (W. L. Gore & Associates, 555 Paper Mill Road Newark, DE 19711), except that it is configured to accept two guidewires. As is known in the art, grip 1000 may be manipulated by a surgeon to longitudinally move central body 710 relative to sleeve 720 for placement of first portion 400 or second portion 500. In certain embodiments, central body 710 and sleeve 70 extend to grip 1000.

Figure 11:
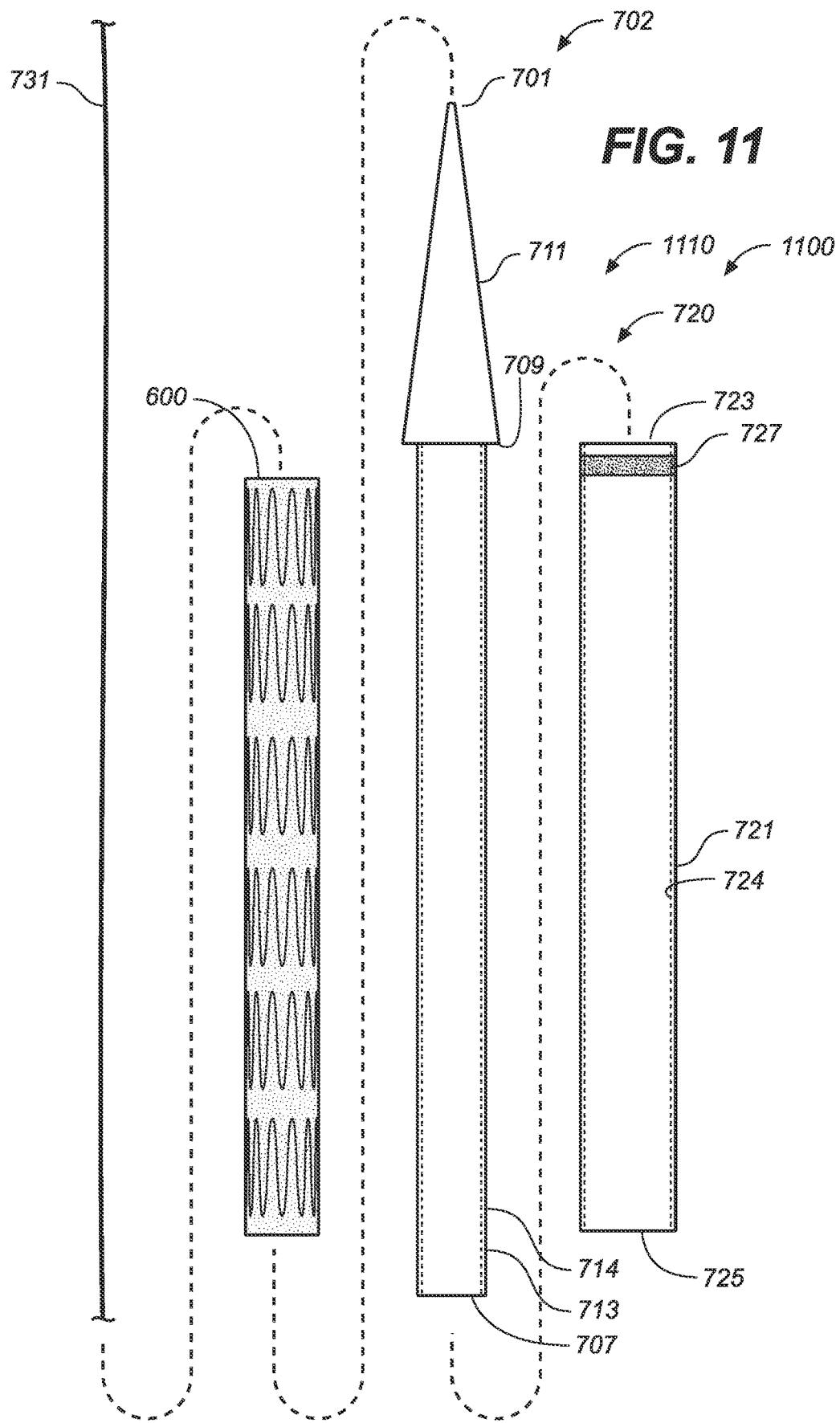
FIG. 11 is an assembly view of a third aortic stent-graft delivery system.
Figure 12:
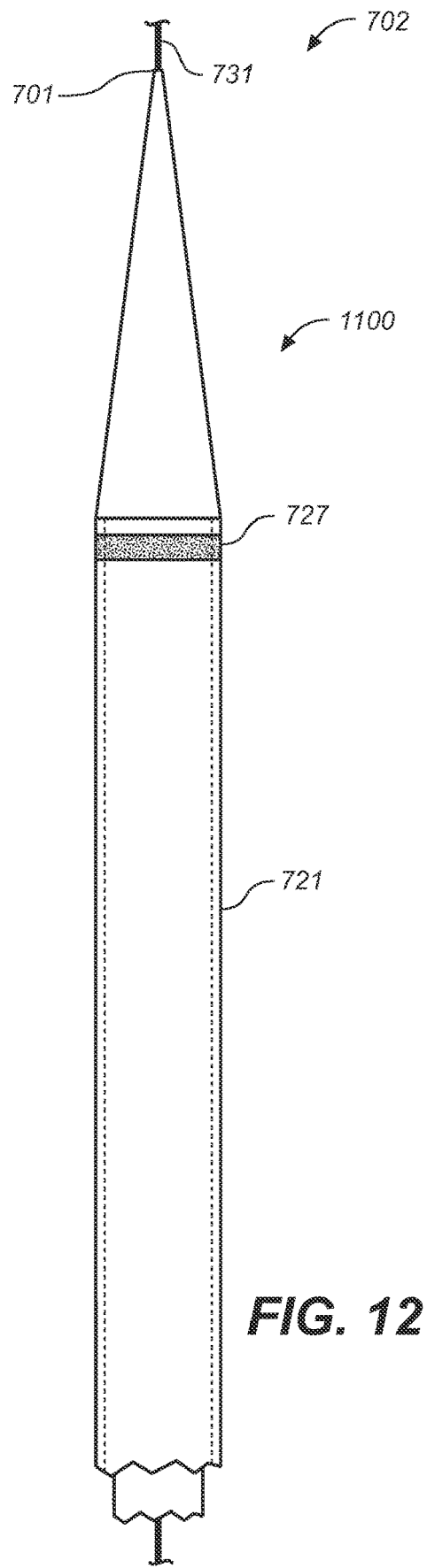
FIG. 12 is a detail perspective posterior view of the third aortic stent-graft delivery system of FIG. 11.

Second delivery system 1100 is illustrated in an assembly view of FIG. 11, in FIG. 12 as a side view of the first delivery system of FIG. 11, and in FIG. 10 as a view of the proximal end of the delivery system of FIG. 11. Second delivery system 1100 may be used to deliver third portion 600 as discussed subsequently. Second delivery system 1100 is generally similar to first delivery system 700, except as explicitly stated.

Second delivery system 1100 includes a central body 1110 and sleeve 720. Central body 1110 is generally similar to opening 701 except that notch 703 and aperture 705 are not required. For the assembly of third portion 600 in second delivery system 1100, cylindrical portion 713 is inserted through the center of the third portion, as shown in FIG. 11. With third portion 600 compressed against cylindrical portion 713, sleeve 720 is placed over the second aortic stent-graft portion with distal end 723 placed against base 709. First guidewire 731 is inserted through proximal end 707, through third portion 600, and through opening 701. As is known in the art, grip 1000 may be manipulated by a surgeon to longitudinally move central body 710 relative to sleeve 720 for placement of third portion 600.

Figure 13:
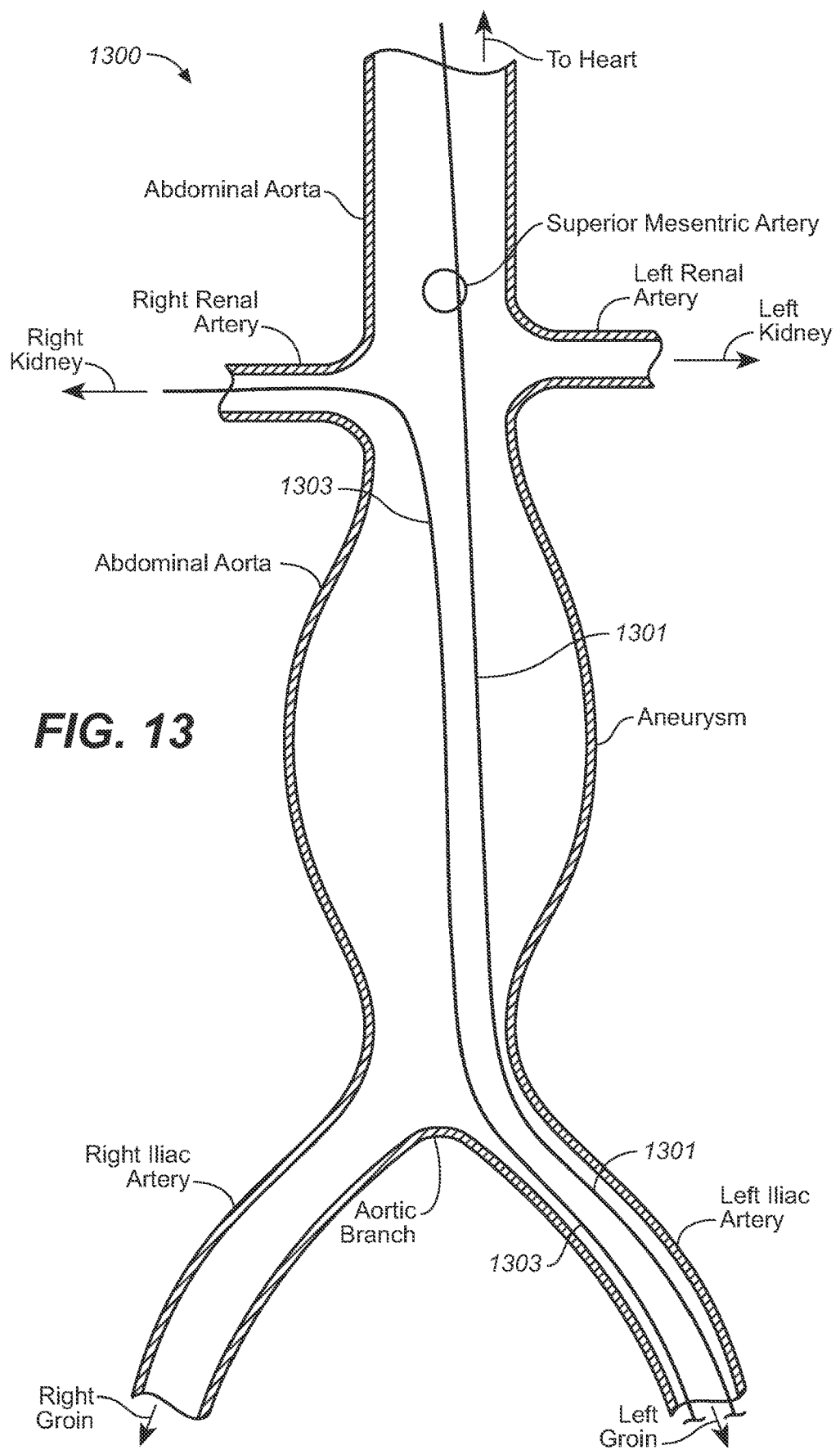
FIGS. 13, 14, 15, and 16 are sequential sectional posterior side views of the delivery of the first portion of the aortic stent-graft of FIG. 4.
Figure 14:
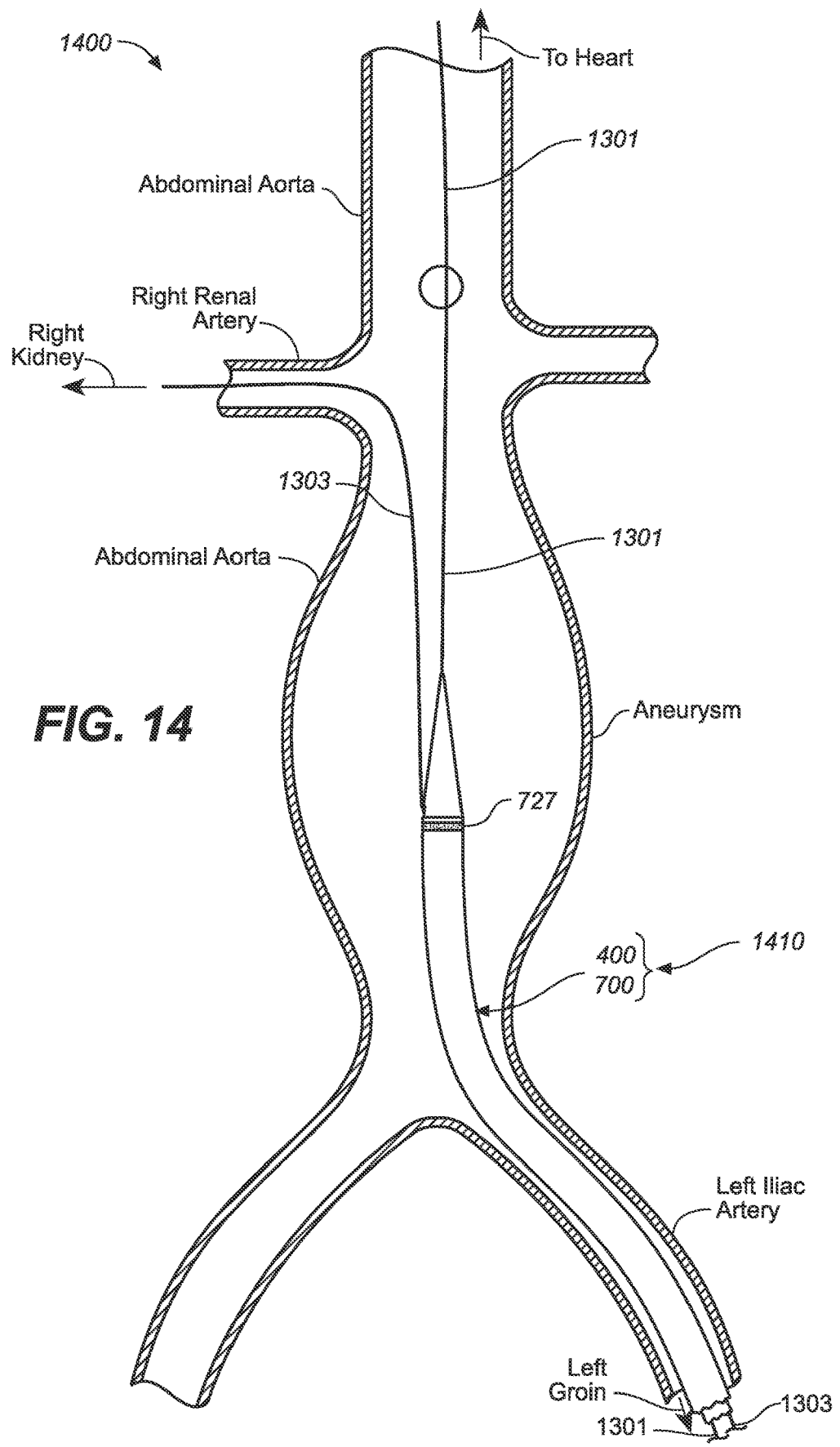
Figure 15:
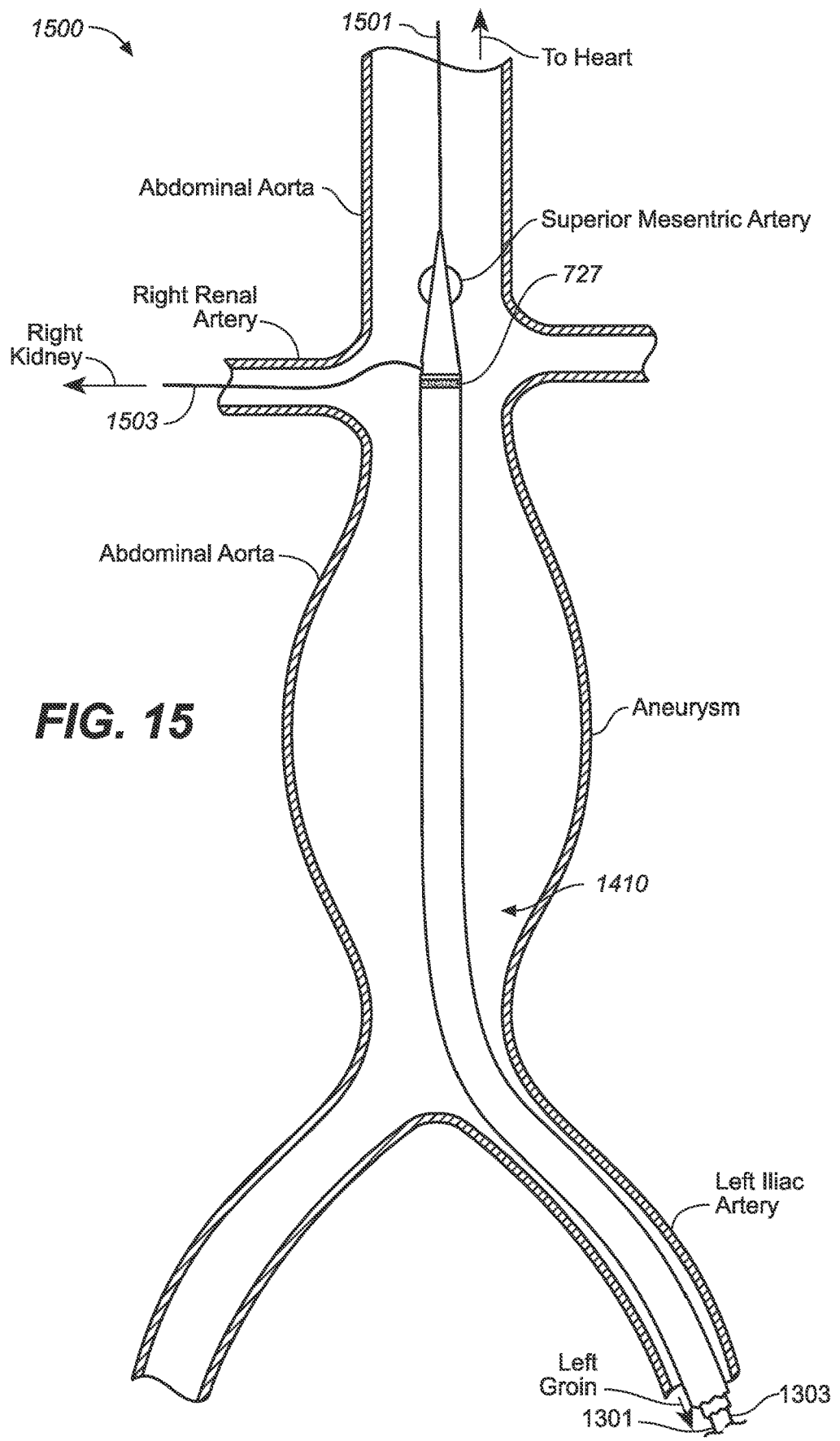
Figure 16:
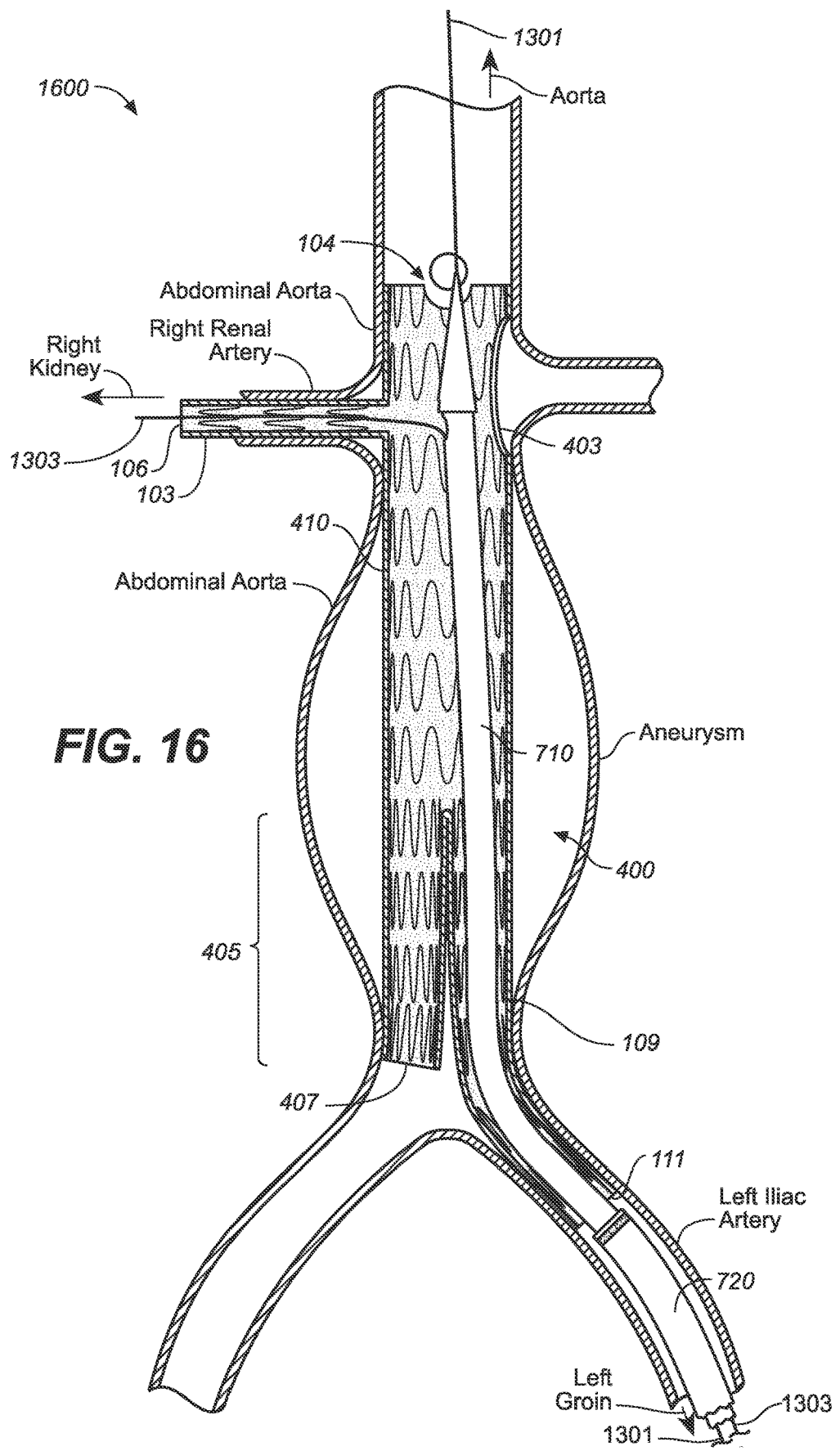
Figure 17:
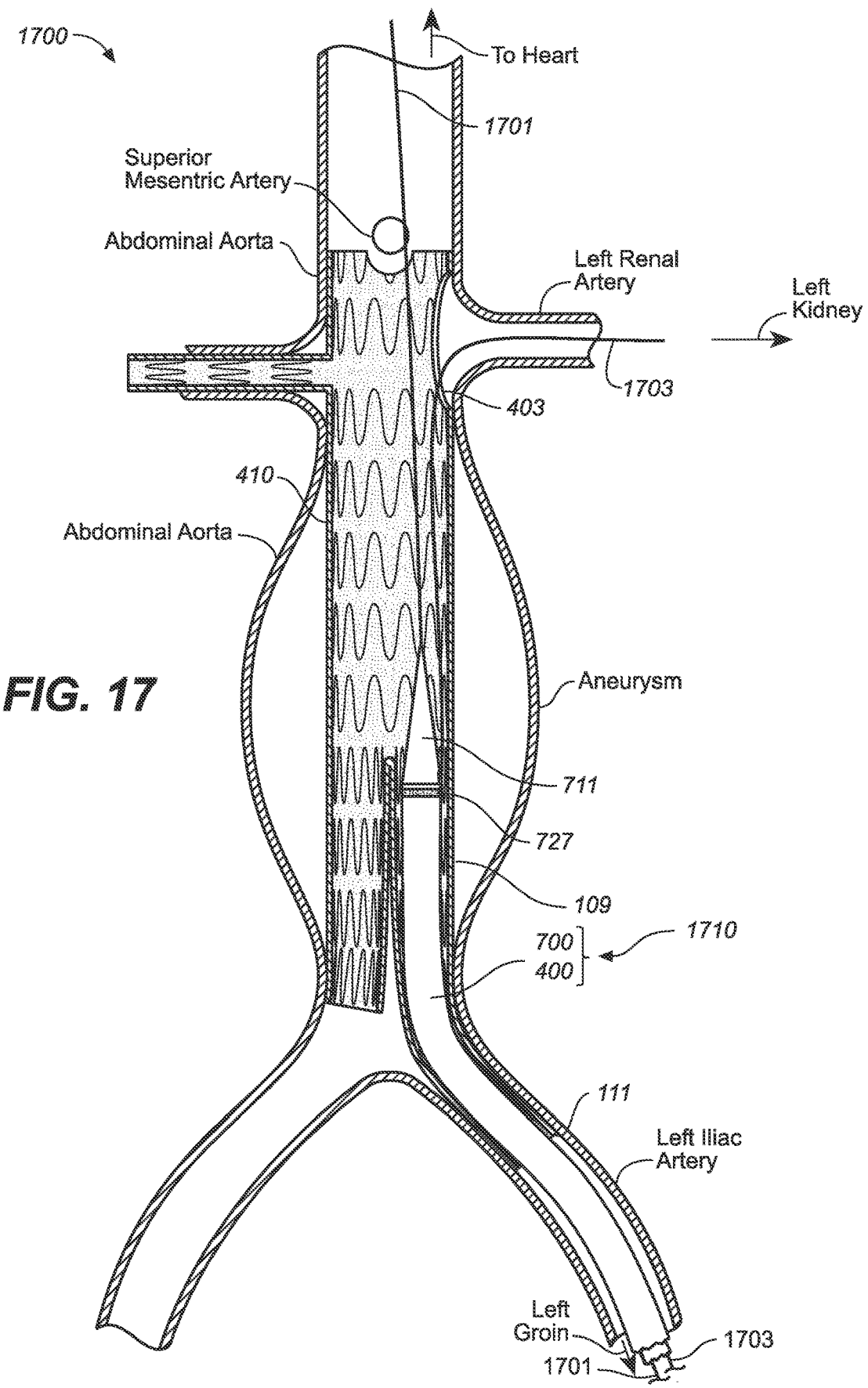
FIGS. 17 and 18 are sequential sectional posterior side views of the delivery of the second portion of the aortic stent-graft of FIG. 5.
Figure 18:
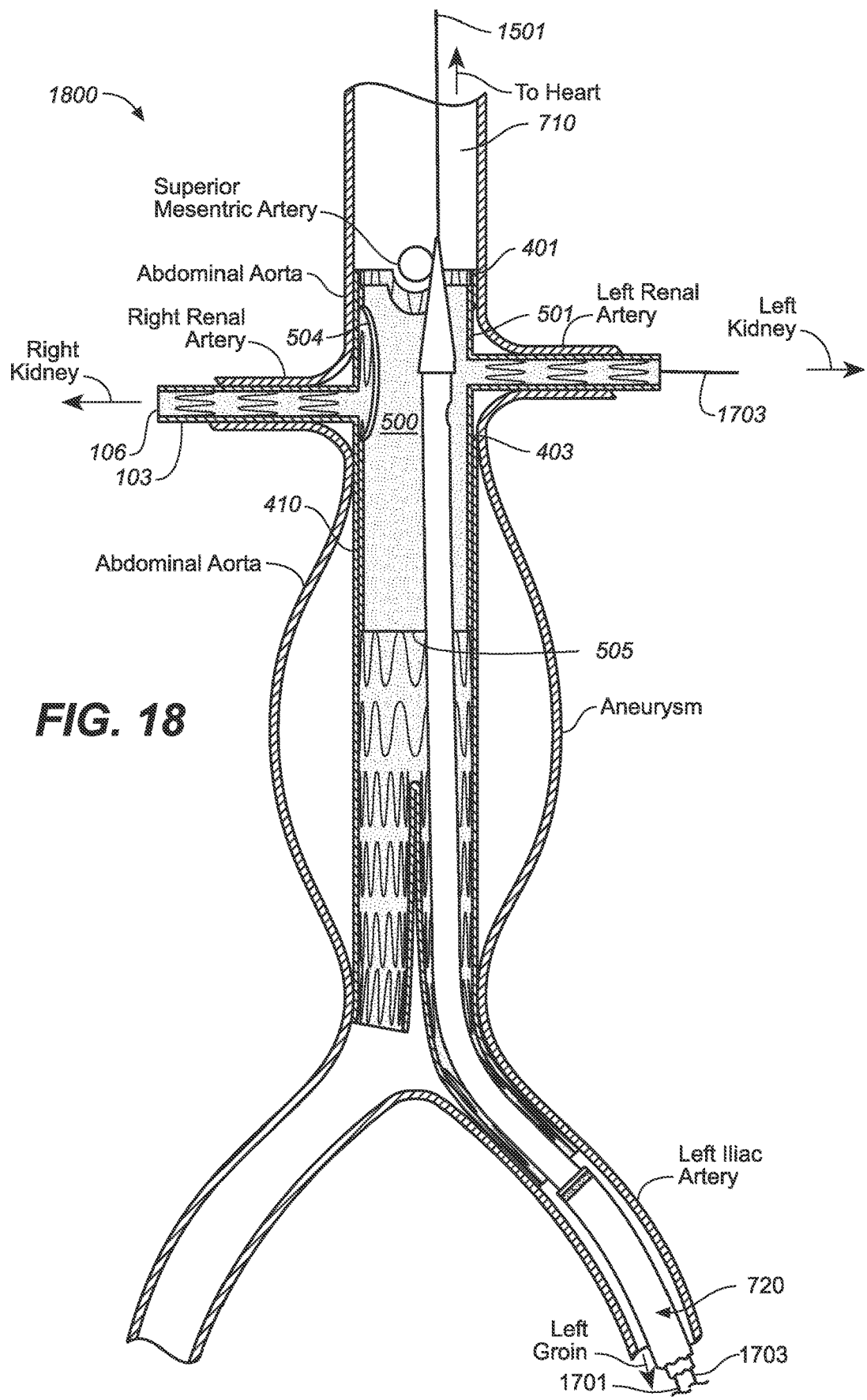
Figure 19:
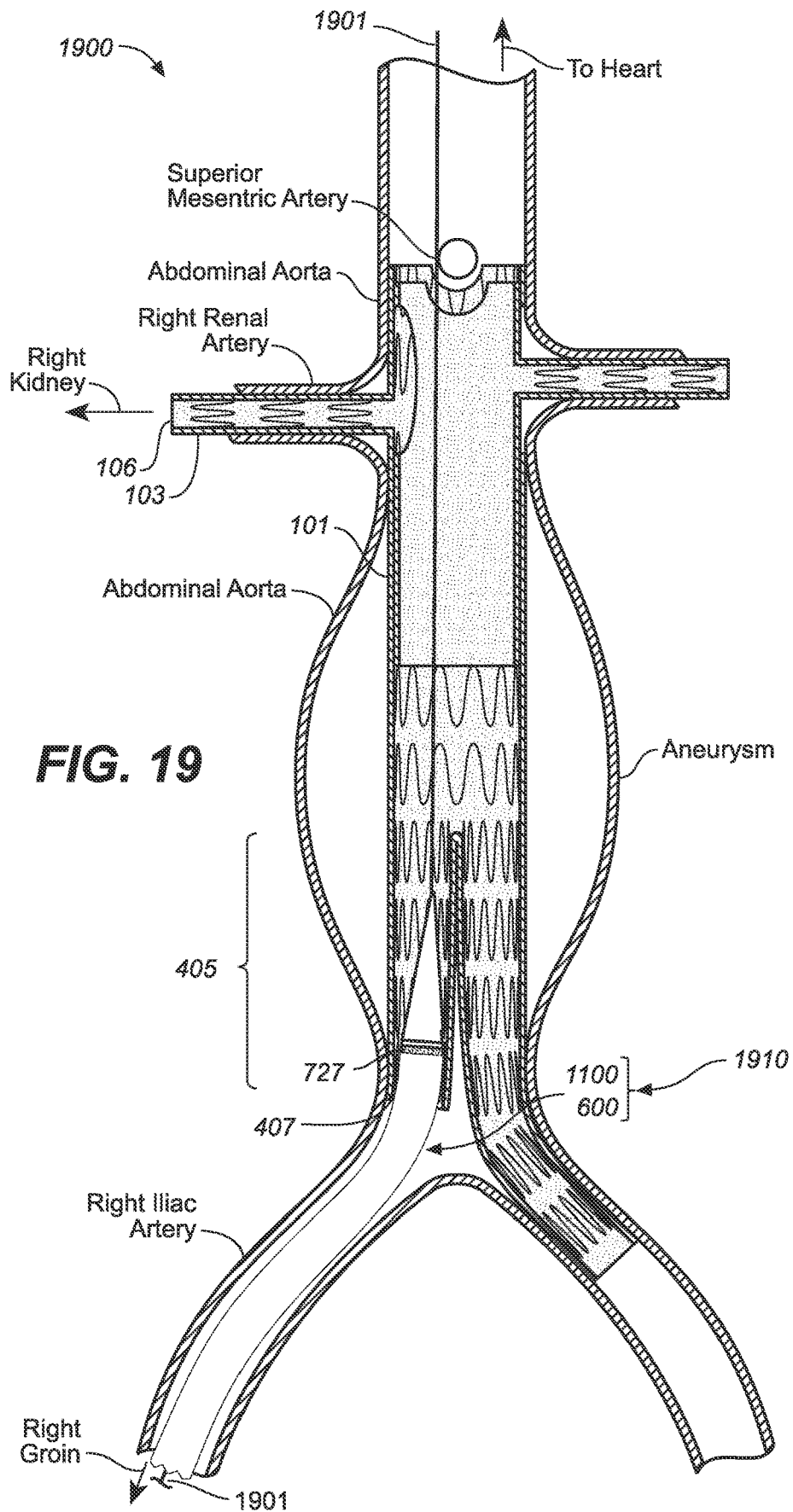
FIG. 19 is a sectional posterior side view of the delivery of the third portion of the aortic stent-graft of FIG. 6.
Figure 20:
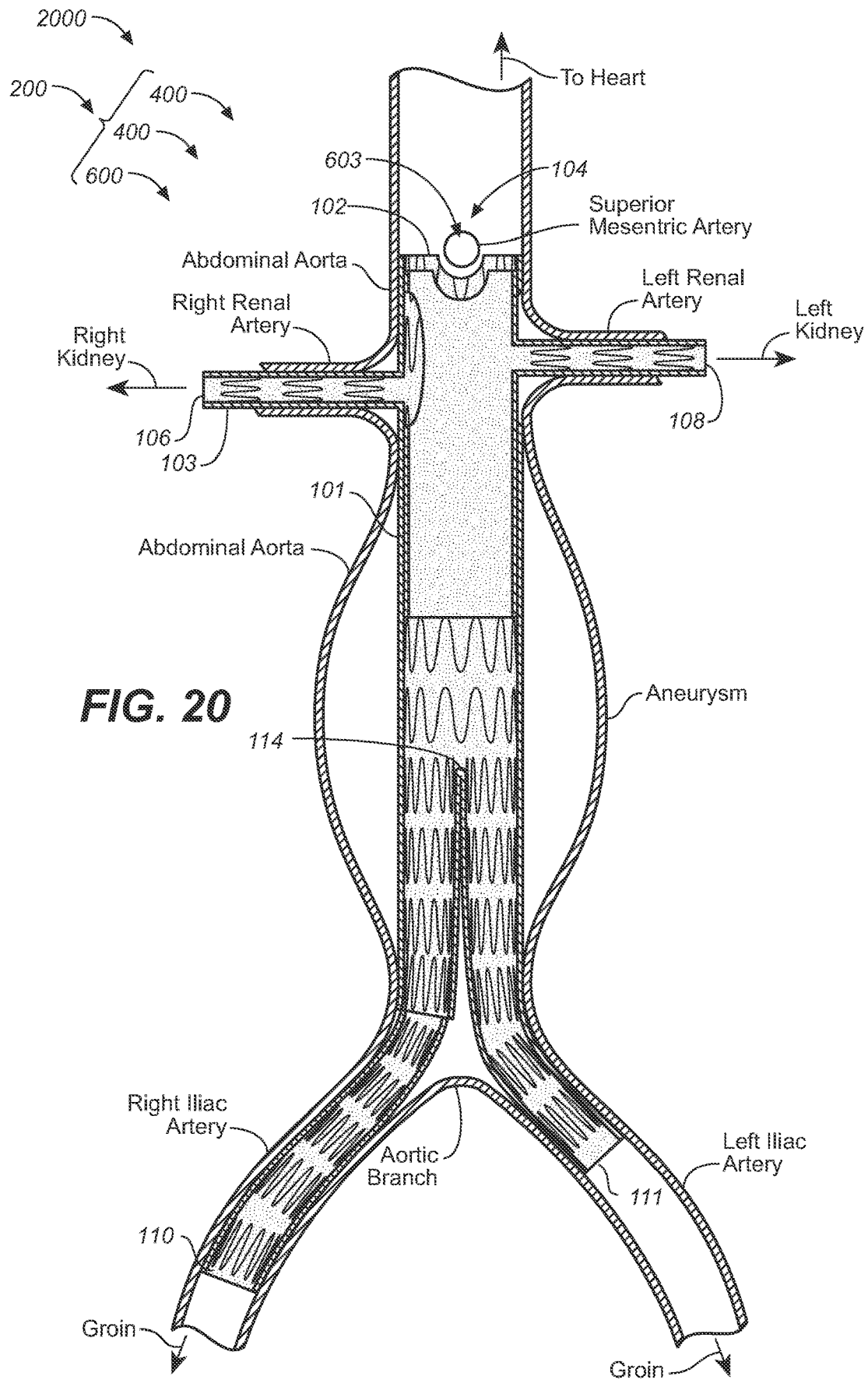
FIG. 20 is a sectional posterior side view of the assembled aortic stent-graft of FIG. 2.

One method of providing aortic stent-graft 200 to the aorta, renal arteries, and iliac arteries of a patient is illustrated in the following sequential sectional views, where FIG. 13 is a sectional view 1300 showing the placement of a first two guidewires for providing first portion 400 in the patient; FIG. 14 is a sectional view 1400 of the insertion of the first portion; FIG. 15 is a second sectional view 1500 of the insertion of the first portion; FIG. 16 is a sectional view 1600 of the insertion of the first portion; FIG. 17 is a sectional view 1700 of the insertion of second portion 500; FIG. 18 is a sectional view 1800 of the insertion of the second portion; FIG. 19 is a sectional view 1800 of the insertion of third portion 600; and FIG. 20 is a sectional view 2000 of the assembled aortic stent-graft.

FIG. 13 shows a location for providing aortic stent-graft 200 as being generally near an aneurysm in the abdominal aorta and extending into the left renal artery, the right renal artery, the left iliac artery, and the right iliac artery. A surgeon performs a first incision in the right groin to provide access to the right iliac artery and a second first incision in the left groin to provide access to the left iliac artery. A pair of guidewires are then inserted through the right iliac artery towards the aorta, where a first guidewire 1301, which is generally similar to first guidewire 731, is inserted into the abdominal aorta and past the renal arteries toward the aorta, and where a second guidewire 1303, which is generally similar to second guidewire 733, is inserted into the abdominal aorta and into the left renal artery.

The anatomic configuration of the aorta, arteries, and aneurysm vary from person to person. Thus, there is a range of diameters of the aorta and arteries, as well as the location of arteries that extend from the abdominal aorta. In addition, there is variation in the relative position of the various arteries. Thus, for example, the left renal artery is generally but not always higher that the right renal artery. The assembly disclosed herein accounts for variations in the location of the renal arteries by guiding the aorta and artery portions of the stent-graft with guidewires and by allowing some longitudinal variation of the upper right branch 103 and upper left branch 105 as described above.

FIG. 14 shows a first portion delivery device 1410 as including first portion 400 in first delivery system 700, as shown in FIGS. 7-10, is guided by first guidewire 1101 past an aneurysm. In certain embodiments, X-rays are absorbed by band 727, and the surgeon uses real-time X-ray imaging to determine when to stop inserting first portion delivery device 1410 into the patient, as shown in FIG. 15.

With first portion delivery device 1410 placed with band 727 near the right renal artery, first portion delivery device 1410 is operated to move central body 710 distally and to move sleeve 720 proximally, as shown in FIG. 16. With central body 710 and sleeve 720 are moved apart, main body 401 expands outwards to the abdominal aorta, with upper left aperture 403 over the opening of the right renal artery, and with upper right branch 103 extending outwards and, guided by second guidewire 733, into the left renal artery, and with notch 104 positioned below the superior mesenteric artery. With first portion 400 inserted into the patient, central body 710, sleeve 720, first guidewire 1301, and second guidewire 1303 are then removed.

Next, a new pair of guidewires are then provided. As shown in FIG. 17 a first guidewire 1701 is inserted from the left groin, through the left iliac artery and lower left branch 109 of first portion 400 towards the aorta, where first guidewire is generally similar to first guidewire 731 or first guidewire 1301. A second guidewire 1703 is inserted through the left groin, through the left iliac artery and lower left branch 109 of first portion 400, through upper left aperture 403 and into the right renal artery, where second guidewire 1703, which is generally similar to second guidewire 733 or second guidewire 1303.

FIG. 17 shows a second portion delivery device 1710 as including second portion 500 in a new first delivery system 700, as shown in FIGS. 7-10, as guided by first guidewire 1701. In certain embodiments, X-rays are absorbed by band 727, and the surgeon uses real-time X-ray equipment to guide insertion of second portion delivery device 1710 to the left renal artery. With second portion delivery device 1710 so placed, the delivery system is operated to move central body 710 distally and to move sleeve 720 proximally, as shown in FIG. 18. As central body 710 and sleeve 720 are moved apart, main body 501 expands outwards to the inner surface of main body 401, with upper right aperture 504 providing access to the right renal artery, and with upper right branch 103 extending outwards and, guided by second guidewire 733, into the left renal artery, as shown in FIG. 18, and with notch 104 providing for the flow of blood between the abdominal aorta to the superior mesenteric artery. Central body 710, sleeve 720, first guidewire 1701 and second guidewire 1703 are then removed.

Next, a new guidewire is provided. As shown in FIG. 19 a guidewire 1901 is inserted from the right groin, through the right iliac artery and opening 407 of first portion 400 towards the aorta, where the guidewire is generally similar to first guidewire 731 or first guidewire 1701.

FIG. 19 shows a third portion delivery device 1910 as including third portion 600 in second delivery system 1100, as shown in FIGS. 10-12, is guided by guidewire 1901 until band 727 is located within opening 407 of first portion 400. In certain embodiments, the surgeon uses real-time X-ray equipment to determine when to stop inserting third portion delivery device 1910 into the patient. With third portion delivery device 1910 placed within lower right branch 405, the delivery system is operated to move central body 710 distally and to move sleeve 720 proximally. As central body 710 and sleeve 720 are moved apart, third portion 600 expands outwards to contact lower right branch 405 and the left iliac artery. Aortic stent-graft 200 has thus been placed within the patient and guidewire 1901 is removed.

FIG. 20 shows the assembled aortic stent-graft 200 in the body of the patient, where the aortic stent-graft seals against the portions of the abdominal aorta, the left renal artery, the right renal artery, the left iliac artery, and the right iliac artery, and thus provides for blood flow between first opening 102 located above the left and right renal arteries, second opening 106 in the left renal artery, third opening 108 in the right renal artery, opening 110 in the left iliac artery, and fifth opening 111 in the right iliac artery. Aortic stent-graft 200 thus effectively provides for blood flow past an aneurysm located between the renal arteries and the aortic branch. In addition, notch 104 and notch 503 are both sized and positioned to provide for blood flow between the abdominal aorta and the superior mesenteric artery, which enters the abdominal aorta between the celiac artery and renal arteries.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Thus, for example, an inventive modular aortic stent-graft may include 2, 3, or more overlapping portions, may not extend to one or more iliac arteries, and may provide other geometries for not occluding branches.

Thus, while there has been described what is believed to be the preferred embodiments of the invention, those skilled in the art will recognize that other and further modifications may be made thereto without departing from the spirit of the invention, and it is intended to claim all such changes and modifications as fall within the scope of the invention. Thus, for example and without limitation:

The invention claimed is:

1. A modular stent-graft sized to fit in an abdominal aorta, a left renal artery, a right renal artery, a left iliac artery, and a right iliac artery of a person, said modular stent-graft comprising:

three portions including a first portion, a second portion, and a third portion, where each of the first portion, the second portion, and the third portion includes a stent-graft sized to be delivered through either the left iliac artery or the right iliac artery and adapted to be deployed within the abdominal aorta, the left renal artery, the right renal artery, the left iliac artery, or the right iliac artery, where the modular stent-graft defines a main body sized to fit in the abdominal aorta, a right upper branch sized to fit in the right renal artery, a left upper branch sized to fit in the left renal artery, a left lower branch sized to fit in the left iliac artery, and a right lower branch sized to fit in the right iliac artery, where each of the three portions of the modular stent-graft overlaps with at least one other portion of the three portions, where the first portion includes the main body, the right upper branch, a first portion aperture in the main body opposite from the right upper branch, and a bifurcation of the main body to form the left lower branch and a first portion branch adapted to extend towards the right iliac artery, where said second portion includes a second portion main body sized to fit within the main body, the left upper branch configured to extend through the first portion aperture and to the left renal artery, and a second portion aperture in the second portion main body positioned to not occlude the right upper branch, and where said third portion includes a third portion main body sized to fit in the first portion branch, where the third portion includes the right lower branch.

2. The modular stent-graft of claim 1, where said first portion, said second portion, and said third portion each include a metal framework or a metal mesh covered by a fabric.

3. The modular stent-graft of claim 2, where said metal framework or said metal mesh includes nickel titanium, and where said fabric is polyester.

4. The modular stent-graft of claim 3, where said polyester is an expanded polytetrafluoroethylene (ePTFE).

5. The modular stent-graft of claim 1, where said modular stent-graft includes a notch positioned and sized to not obstruct a superior mesenteric artery of the person.

6. The modular stent-graft of claim 1, where a longitudinal position of the right upper branch and the left upper branch is adjustable according to size and location of the first portion aperture and the second portion aperture.

7. A method for repairing an aortic aneurysm of a person with a modular stent-graft sized to fit within an abdominal aorta, a right renal artery, a left renal artery, a left iliac artery, and a right iliac artery of the person, where said modular stent-graft includes three overlapping portions including a first portion, a second portion, and a third portion, where the modular stent-graft includes defines a main body sized to fit in the abdominal aorta, a right upper branch of the main body-sized to fit in the right renal artery, a left upper branch of the main body-sized to fit in the left renal artery, a left lower branch of the main body sized to fit in the left iliac artery, and a right lower branch of the main body-sized to fit in the right iliac artery, where the first portion includes the main body, the right upper branch, and a bifurcation of the main body to form the left lower branch and a first portion branch extending towards the right iliac artery, where said second portion includes a second portion main body sized to fit within the main body; and the left upper branch, and where said third portion includes a third portion main body sized to fit in the first portion branch, where the third portion includes the right lower branch, said method comprising:

a first incising of a left groin and a left femoral artery of the person;

a second incising of a right groin and a right femoral artery of the person;

deploying the first portion through the first incision to the abdominal aorta at the aneurysm and to the right renal artery;

deploying the second portion through the first incision and to an interior of the deployed main body and to the left renal artery; and deploying the third portion through the second incision and to an interior of the deployed first portion branch and to the right iliac artery.

8. The method of claim 7, where said first portion, said second portion, and said third portion each include a metal framework or a metal mesh covered by a fabric.

9. The method of claim 7, where said deploying the first portion includes inserting a first guidewire through the first incision and into the abdominal artery past the renal arteries and inserting a second guidewire through the first incision and into the right renal artery, where the first guidewire extends through the main body and where the second guidewire extends through the main body and through the right upper branch.

10. The method of claim 9, where said deploying the second portion includes inserting a third guidewire through the first incision and into the abdominal artery past the renal arteries and inserting a fourth guidewire through the first incision and into the left renal artery, where the third guidewire extends through the second portion main body and where the fourth guidewire extends through the second portion main body and through the left upper branch.

11. The method of claim 10, where said deploying the third portion includes inserting a fifth guidewire through the second incision and into the abdominal artery past the renal arteries, where the fifth guidewire extends through the third portion main body.

12. The method of claim 10, where a longitudinal position of the deployed first portion branch and the deployed second portion branch along the abdominal aorta is determined when the first portion and the second portion are deployed.

13. The method of claim 10, where said modular stent-graft includes a notch positioned and sized to not obstruct a superior mesenteric artery of the person.

14. The method of claim 7, where the first portion further includes a first portion aperture in the main body positioned opposite from the right upper branch, where the second portion further includes a second portion aperture in the second portion main body opposite from the left upper branch, and where said deploying the second portion further includes deploying with the left upper branch extending through the first portion aperture and into the left renal artery, and with the second portion aperture not occluding the right upper branch.

\* \* \* \* \*